United States Patent
Levecke

(10) Patent No.: US 8,496,994 B2
(45) Date of Patent: Jul. 30, 2013

(54) METHOD FOR PROVIDING FRAGRANCE TO A SUBSTRATE; FRAGRANCE-CONTAINING SUBSTRATE

(75) Inventor: Bart Levecke, Mechelen (BE)

(73) Assignee: Raffinerie Notre Dame-Orafti S.A. (BE)

( * ) Notice: Subject to any disclaimer, the term of this patent is extended or adjusted under 35 U.S.C. 154(b) by 674 days.

(21) Appl. No.: 12/596,798

(22) PCT Filed: May 15, 2008

(86) PCT No.: PCT/EP2008/003913
§ 371 (c)(1),
(2), (4) Date: Oct. 20, 2009

(87) PCT Pub. No.: WO2008/141765
PCT Pub. Date: Nov. 27, 2008

(65) Prior Publication Data
US 2010/0196732 A1    Aug. 5, 2010

(30) Foreign Application Priority Data

May 18, 2007 (DE) .................... 07009981
May 18, 2007 (DE) .................... 07009982
Aug. 27, 2007 (DE) .................... 07016724

(51) Int. Cl.
*B32B 23/04* (2006.01)

(52) U.S. Cl.
USPC ........ 427/389.9; 427/391; 427/394; 427/395; 427/412; 428/532; 510/101; 510/276; 510/474

(58) Field of Classification Search
USPC .......... 510/101, 276, 474; 428/532; 427/391, 427/394, 395, 412, 389.9
See application file for complete search history.

(56) References Cited

U.S. PATENT DOCUMENTS

| 4,585,858 A | 4/1986 | Molotsky ............ 3/4.1 |
| 5,425,887 A * | 6/1995 | Lam et al. ............ 510/520 |
| 5,804,538 A | 9/1998 | Wei et al. ............ 510/101 |
| 5,858,959 A * | 1/1999 | Surutzidis et al. ............ 510/507 |
| 2007/0105743 A1 | 5/2007 | Booten et al. ............ 510/476 |

FOREIGN PATENT DOCUMENTS

| EP | 0 638 589 | 8/1994 |
| EP | 0703243 | 3/1996 |
| EP | A-792888 | * 8/1997 |
| EP | 0 792 888 | 9/1997 |
| EP | 1 614 743 | 11/2003 |
| EP | 1 380 284 | 1/2004 |
| EP | A-1380284 | * 1/2004 |
| EP | A-1541117 | * 6/2005 |
| EP | 1 600 151 | 11/2005 |
| EP | 1 541 117 | 6/2008 |
| GB | 601374 | 5/1948 |
| GB | 806935 | 1/1959 |
| JP | H03197409 | 8/1991 |
| WO | WO 97/48374 | 12/1997 |
| WO | WO 98/12291 | 3/1998 |
| WO | WO-A-9812291 | * 3/1998 |
| WO | WO9964549 | 12/1999 |
| WO | WO0144303 | 6/2001 |
| WO | WO 03/031043 | 4/2003 |
| WO | WO-A-03031043 | * 4/2003 |

* cited by examiner

*Primary Examiner* — Leszek Kiliman
(74) *Attorney, Agent, or Firm* — Hayes Soloway P.C.

(57) ABSTRACT

The invention relates to a method for providing fragrance to a substrate, comprising the steps of: a) treating the substrate with a fragrance-containing composition; and b) treating the substrate with a fixative compound or mixture of fixative compounds selected from the group consisting of: a fructan; a starch hydrolysate having a dextrose equivalent ranging from 1 to 50; a hydrophobically modified fructan; and a hydrophobically modified starch hydrolysate, whereby step b) may be executed prior to, simultaneously with, and/or subsequent to the execution of step a). The invention further relates to fragrance-containing compositions and substrates.

10 Claims, 2 Drawing Sheets

METHOD FOR PROVIDING FRAGRANCE TO A SUBSTRATE; FRAGRANCE-CONTAINING SUBSTRATE

Figure 1:
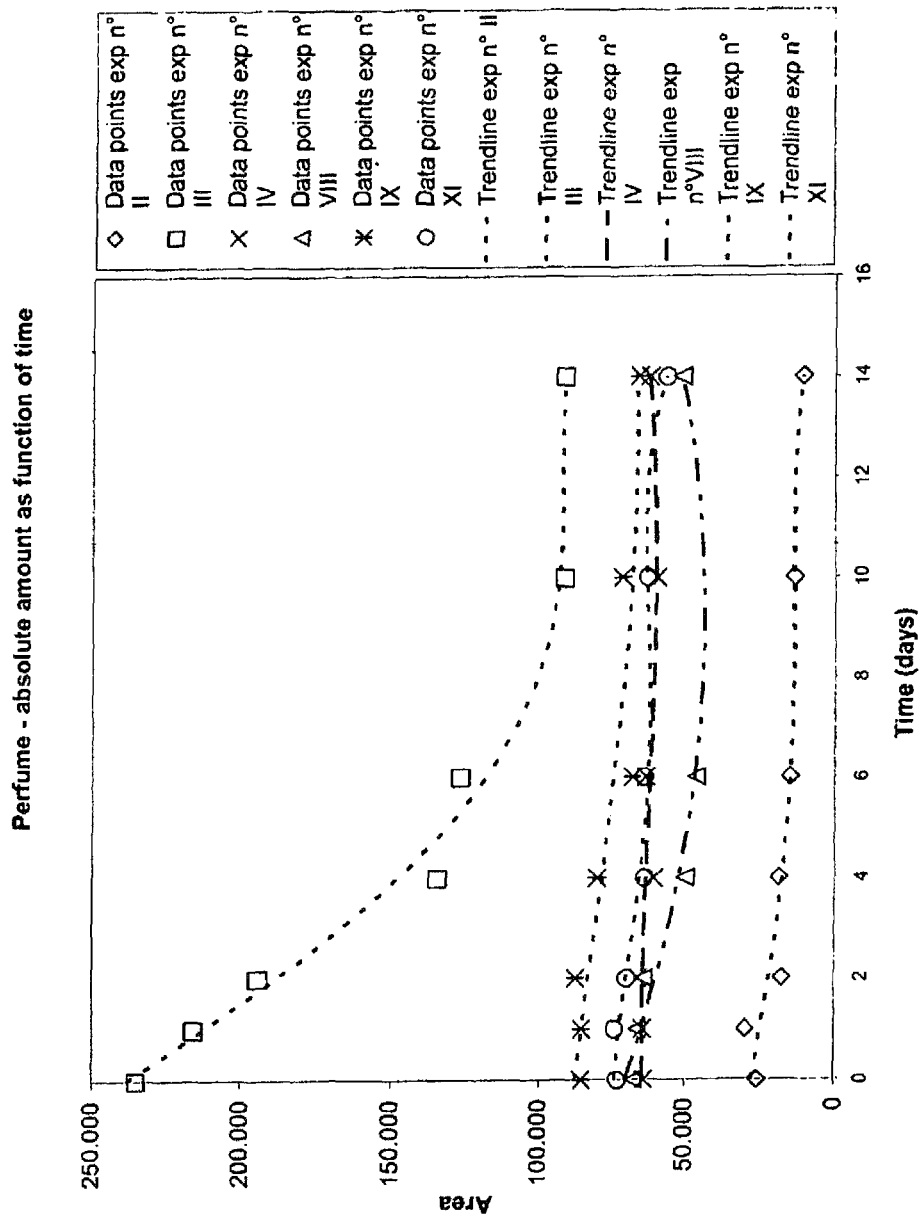

The invention relates to a method for providing fragrance to a substrate, and to fragrance-containing substrates.

People enjoy it when a substrate carries with it the smell of a fragrance. Examples are abundant, and range from scented letters to washed textile fabric and so forth. Textile fabric is referred to herein in short as textile. To provide the pleasing smell of freshly washed textile or to perfume a textile fabric, the textile is commonly treated with a perfume or fragrance. In view thereof, washed and dried textile was previously stored in the presence of an odorous soap, such as soap of Marseille, or in the presence of dried, odorous herbs and/or flowers, such as lavender. More recently, fragrances, including extracts of herbs and flowers, and semi-synthetic and synthetic fragrances, have been put into use to impart to laundry a scent of freshness or of a desired perfume through a washing cycle.

Various methods and compositions have already been developed to provide fragrance to laundry through a washing cycle and to maintain fragrance for a certain period of time after drying of the washed laundry.

Within the context of the present invention, the term fragrance is meant to embrace also the meaning of the term perfume; moreover, depending on context and as is customary, the term fragrance is used for both a fragrance compound itself as well as for a fragrance effect.

In a known approach to impart fragrance to textile, the fragrance is added through the detergent composition during the washing cycle, typically in a concentration ranging from 0.05% to 3% (% w/w on total composition). However, a large part of the added fragrance is lost via the wash waters, which largely reduces the efficiency of the amount of the added fragrance. In another known and presently the most common approach, the fragrance is added via a laundry softener composition, typically in a concentration ranging from 0.05% to 3% (% w/w on total composition), at the end of the washing cycle, before the drying step. According to this method, losses of fragrance in the wash waters from the treatment of the laundry with a detergent composition are obviously avoided, but there is still a significant amount of the fragrance added through the laundry softener composition lost via the rinsing waters of this step. So, the losses of fragrance via the rinsing waters also considerably reduce the efficiency of added fragrance.

Furthermore, often the effect of the imparted fragrance on washed and dried textile is short-lasting, whereas preferably a long-lasting fragrance is desired.

In case a higher concentration of fragrance would be used in laundry compositions to compensate the losses of fragrance occurring during the washing cycle in order to end up the washing cycle with a desired high amount of fragrance adsorbed to the textile, the cost of such composition would be noticeably and often unacceptably increased and the initial smell of such laundry compositions, particularly of laundry powders, would be unacceptably strong.

A method of providing an improved transfer of fragrance from laundry compositions to laundry during a washing cycle is disclosed in EP 1614743 A1. According to EP 1614743 A1, a fragrance incorporated into a film or sheet composed of water-soluble cellulose derivatives and/or polysaccharides is added at the soaking stage prior to commencing the washing. The film or sheet may be added directly to the laundry in a washing machine in the detergent drawer to replace the fabric softener. When added directly to the laundry, the film is used alone or can be associated with detergent tablets or powder, as a two-in-one product. The polymer film or sheet can contain more fragrance than is usually present in a normal laundry detergent charge, and the method is disclosed to provide enhanced olfactory performances over a certain period of time, namely providing a persisting high level of fragrance for more than 5 days. However, this known method suffers from disadvantages, including the fact that the films or sheets containing the fragrance have to be prepared separately and added as a separate composition to the washing cycle, associated or not with the detergent composition, which may render dosing of the amount of fragrance to be added to a washing cycle, difficult. Furthermore, EP 1614743 A1 is silent about the long-lasting olfactory effect imparted by the method after more than 5 days.

Thus, having regard on the one hand to the demand for laundry that after a washing cycle presents a pleasing scent of freshly washed laundry or of a desired perfume, and the demand that washed and dried textile presents long-lasting desired olfactory effects, and on the other hand, to the disadvantages of the known methods and compositions for providing a fragrance to textile fabrics during a washing cycle, there remains a need for convenient methods and compositions for use in these methods that respond to said demands.

Similarly, there remains a need to improve the administering and fixation of a fragrance onto other substrates such as paper or paper-based products.

It is thus an objective of the present invention to provide a convenient, alternative or improved method for providing fragrance, in particular long-lasting fragrance, to a substrate.

This objective is achieved by a method for providing fragrance to a substrate, comprising the steps of:
a) treating the substrate with a fragrance-containing composition; and
b) treating the substrate with a fixative compound or mixture of fixative compounds selected from the group consisting of:
   a fructan;
   a starch hydrolysate having a dextrose equivalent ranging from 1 to 50;
   a hydrophobically modified fructan; and
   a hydrophobically modified starch hydrolysate,
whereby step b) may be executed prior to, simultaneously with, and/or subsequent to the execution of step a).

An advantage of the method of the invention, when applied to the washing cycle of textile, is that an efficient and improved transfer of the fragrance from the laundry composition to the laundry compared to prior art methods can be achieved, as well as an improved fragrance fixation.

In the method of the invention, fragrance is provided to a substrate. As indicated above, the term fragrance embraces the term perfume, as well as their olfactory effects. The substrate to which the fragrance is provided may be any substrate of which it is, or may be desirable to provide a fragrance to. In one preferred embodiment, the substrate has a fibrous or porous structure. It may be beneficial if the surface substrate shows a polarity or even comprises charged groups. Suitable substrates include all types of textile, all types of paper, wood, and plastic. Suitable substrates, however also include skin or hair of mammals, preferably of humans or companion animals such as a dog or a cat.

According to the invention, the substrate is in a step a) treated with a fragrance-containing composition. The treatment of step a) is as such a known step and may be executed in a variety of ways. Examples of treatments according to step a) are the spraying of a liquid fragrance-containing composition onto the substrate, or the introduction of a fragrance-containing composition into a washing cycle.

The method of the invention further comprises a step b). Step b), which may be executed prior to, simultaneously with, and/or subsequent to the execution of step a), also pertains to the treatment of the substrate; this treatment involves the bringing into contact of a fixative compound or mixture of fixative compounds with the substrate. As meant herein, the term fixative compound means a compound that enhances the transport and/or the adhesion of a fragrance to the substrate. According to the invention, the fixative compound or mixture of fixative compounds is/are selected from the group consisting of a fructan, a starch hydrolysate having a dextrose equivalent ranging from 1 to 50, a hydrophobically modified fructan, and a hydrophobically modified starch hydrolysate.

The term fructan as used herein has its common meaning of being a generic term that relates to a polydisperse carbohydrate material consisting mainly of fructosyl-type monomeric units connected via fructosyl-fructose links with optionally a glucose starting moiety. The meaning of fructan encompasses the more specific compounds inulin—wherein the fructosyl—fructose links are mainly of the β(2→1) type—and levan—wherein the fructosyl-fructose links are mainly of the β(2→6) type. Both inulins and levans can be linear or branched. The meaning of the term inulin on its part encompasses the compounds known as oligofructoses; typical of oligofructose is that the degree of polymerisation (DP) ranges from 2 to 10. Preferably, the fructan is inulin having a DP ranging from 2 to 100.

Starch hydrolysates are known in the art. They are a polydisperse mixture of linear and/or branched polymers composed of glucosyl-type monomeric units, and are prepared by conventional processes, for example by acidic or enzymatic partial hydrolysis from various starch sources, for example corn, potato, tapioca, rice, sorghum and wheat, and are commercially available in various grades. Starch hydrolysates are composed of polyglucose molecules which, due to a terminal glucosyl unit, present reducing power which is expressed, on dry product basis, in dextrose equivalent (D.E.), D-glucose having per definition a D.E. of 100. The D.E. value is a measure for the extent of the hydrolysis of the starch and thus also a relative indication of the average degree of polymerisation of the polyglucose (saccharide) molecules of the hydrolysate. Starch hydrolysates are usually defined by their D.E. value. Starch hydrolysates with a very high D.E. are typically named glucose syrup, whereas starch hydrolysates with a low D.E. are usually named maltodextrin. Starch hydrolysates with intermediate D.E. values—e.g. ranging from 20 to 60—are sometimes named maltodextrin and sometimes glucose syrup, depending on the source. Starch hydrolysates that are suitable as the polysaccharide in accordance with the present invention, including commercial grade products, have a D.E. ranging from 1 to 47 or even 50, preferably from 1 to 30. They are available for many sources, for example as Glucidex® products (trade name from Roquette Fréres, France).

The terms hydrophobically modified fructan and hydrophobically modified starch hydrolysate as used herein have the meaning of being a derivative of a fructan or starch hydrolysate in which a portion of the hydrogen atoms of —OH groups of the fructosyl or glucosyl units has been substituted by a hydrophobic group. Such substitutions are as such known in the art. Preferably, the hydrophobically modified fructan and/or the hydrophobically modified starch hydrolysate are according to formula (I)

$$S_{AC}(-M)_s \quad (I)$$

wherein
S$_{AC}$ represents:
(i) an inulin moiety with a degree of polymerisation (DP) ranging from 2 to 100; or
(ii) a starch hydrolysate moiety with a dextrose equivalent (D.E.) value ranging from 1 to 50, (-M) represents a hydrophobic moiety, substituting at least one hydrogen atom of a hydroxyl group of S$_{AC}$, whereby (-M) is selected from the group consisting of:
an alkylcarbamoyl radical of formula $R_1$—NH—CO—,
an alkenyl-carbamoyl radical of formula $R_2$—NH—CO—,
an alkylcarbonyl radical of formula $R_1$—CO—,
an alkenylcarbonyl radical of formula $R_2$—CO—,
an alkyl radical of formula $R_1$—,
an alkenyl radical of formula $R_2$—, and
a hydroxyalkyl radical of formula $R_3$—,
wherein:
$R_1$ represents a linear or branched alkyl group with 4 to 22 carbon atoms,
$R_2$ represents a linear or branched alkenyl group with 4 to 22 carbon atoms, and
$R_3$ represents a linear or branched hydroxyalkyl group with 4 to 22 carbon atoms of formula —CHR'—CHOH—R", wherein R' is hydrogen or a linear or branched alkyl radical and R" is a linear or branched alkyl radical; and
s represents the number of hydrophobic moieties (-M) attached to S$_{AC}$, expressed as the number average degree of substitution (av. DS) per monomeric unit contained in S$_{AC}$ and which ranges from 0.01 to 1.0.

Fructan derivatives, in particular inulin derivatives, as well as starch hydrolysate derivatives of formula (I) wherein (-M) represents an alkylcarbamoyl radical of formula $R_1$—NH—CO—, or an alkenylcarbamoyl radical of formula $R_2$—NH—CO—, wherein $R_1$ and $R_2$ represent a linear or branched alkyl group, respectively alkenyl group, with 4 to 22 carbon atoms, are known in the art and for example disclosed in WO 99/064549 and WO 01/44303. They can be conventionally prepared by reaction of inulin, respectively a starch hydrolysate, with an alkylisocyanate or alkenylisocyanate of respectively formula $R_1$—N=C=O and $R_2$—N=C=O wherein $R_1$ and $R_2$ have the meanings defined above.

A typically suitable inulin derivative of formula (I) is for example inulin laurylcarbamate, which is commercially available as INUTEC®SP1 (trade name) from Orafti, Belgium, and which is based on inulin having an average degree of polymerisation (DP) ranging from 23 to 27.

A typically suitable starch hydrolysate derivative of formula (I) is for example a carbamate derived from a starch hydrolysate having a D.E. value from 2 to 19 wherein the $R_1$ alkyl group of the alkylcarbamoyl radical or the $R_2$ alkenyl group of the alkenylcarbamoyl radical is a linear group containing from 8 to 18 carbon atoms.

Fructan derivatives, in particular inulin derivatives, and starch hydrolysate derivatives of formula (I) wherein (-M) represents an alkylcarbonyl radical of formula $R_1$—CO— or an alkenylcarbonyl radical of formula $R_2$—CO—, wherein $R_1$ and $R_2$ represent a linear or branched alkyl, respectively alkenyl group with 4 to 22 carbon atoms, are known in the art and can be prepared by conventional esterification reactions, for example by reaction of inulin, respectively a starch hydrolysate, with an anhydride of formula $R_4$—CO—O—CO—$R_4$ or $R_4$—CO—O—CO—CH$_3$, or an acid chloride of formula $R_4$—CO—Cl (wherein $R_4$ represents respectively a radical $R_1$ or $R_2$ having the meanings given above). Such esterification reactions and said inulin derivatives and starch hydrolysate derivatives are for example disclosed in EP 0792888, EP 0703243, GB 601374, GB 806935 and/or JP 3-197409.

Inulin derivatives and starch hydrolysate derivatives of formula (I) wherein (-M) represents an alkyl radical of formula $R_1$ or an alkenyl radical of formula $R_2$, $R_1$ and $R_2$ being defined above, are known in the art. They can be prepared by conventional etherification or alkylation reactions, for example by reaction, in the presence of a base, of inulin, respectively a starch hydrolysate, with an alkyl halide of formula $R_1$—X, or an alkenyl halide of formula $R_2$—X, or an alkyl sulphate of formula $R_1$—O—$SO_2$—O—$R_1$, or an alkenyl sulphate of formula $R_2$—O—$SO_2$—O—$R_2$, wherein $R_1$ and $R_2$ have the meanings defined above and X represents a chloride, bromide or iodide anion, or an other leaving group. Such alkylation reactions and said inulin derivatives and starch hydrolysate derivatives are for example disclosed in GB 601374 and/or GB 806935.

Inulin derivatives and starch hydrolysate derivatives of formula (I) wherein (-M) represents a hydroxyalkyl radical, preferably a 2-hydroxyalkyl radical, of formula $R_3$ ($R_3$ being defined above), are also known in the art and can be prepared conventionally, for example by reaction of inulin, respectively a starch hydrolysate, in the presence of an alkaline catalyst, with a linear or branched epoxyalkane, preferably a 1,2-epoxyalkane containing from 4 to 22 carbon atoms, as for example disclosed in EP 0638589, GB 601374 and U.S. Pat. No. 4,585,858.

The saccharide moieties of the inulin and starch hydrolysate derivatives according to formula (I), can be substituted by one or more alkylcarbamoyl moieties of formula $R_1$—NH—CO—, alkenylcarbamoyl moieties of formula $R_2$—NH—CO—, alkylcarbonyl moieties of formula $R_1$—CO—, alkenylcarbonyl moieties of formula $R_2$—CO—, alkyl moieties of formula $R_1$—, alkenyl moieties of formula $R_2$—, or hydroxyalkyl moieties of formula $R_3$, ($R_1$, $R_2$ and $R_3$ being defined above), in which all $R_1$ groups, respectively all $R_2$ and all $R_3$ groups, can be the same or different, or by any combination thereof.

The value of s (average DS) of the derivatives of formula (I) can range from 0.01 to 1.0, and preferably ranges from 0.02 to 0.5, more preferably from 0.05 to 0.5, most preferably from 0.05 to 0.3.

Typical examples of hydrophobically modified saccharides of formula (I) that are suitable in accordance with the present invention are listed in Table 1 below.

TABLE 1

Hydrophobically modified saccharides of formula (I)

| Nr | Type[1] | (-M)[2] | R[3] | s[4] |
|---|---|---|---|---|
| 1 | a | R—NH—CO | $CH_3(CH_2)_7$— | 0.02 |
| 2 | a | R—NH—CO | $CH_3(CH_2)_7$— | 0.08 |
| 3 | a | R—NH—CO | $CH_3(CH_2)_7$— | 0.09 |
| 4 | a | R—NH—CO | $CH_3(CH_2)_7$— | 0.2 |
| 5 | a | R—NH—CO | $CH_3(CH_2)_{11}$— | 0.07 |
| 6 | a | R—NH—CO | $CH_3(CH_2)_{11}$— | 0.09 |
| 7 | a | R—NH—CO | $CH_3(CH_2)_{11}$— | 0.1 |
| 8 | a | R—NH—CO | $CH_3(CH_2)_{11}$— | 0.1 |
| 9 | a | R—NH—CO | $CH_3(CH_2)_{11}$— | 0.1 |
| 10 | a | R—NH—CO | $CH_3(CH_2)_{11}$— | 0.12 |
| 11 | a | R—NH—CO | $CH_3(CH_2)_{11}$— | 0.15 |
| 12 | a | R—NH—CO | $CH_3(CH_2)_{11}$— | 0.21 |
| 13 | a | R—NH—CO | $CH_3(CH_2)_{11}$— | 0.3 |
| 14 | a | R—NH—CO | $CH_3(CH_2)_{15}$— | 0.21 |
| 15 | a | R—NH—CO | $CH_3(CH_2)_{17}$— | 0.023 |
| 16 | a | R—NH—CO | $CH_3(CH_2)_{17}$— | 0.054 |
| 17 | a | R—NH—CO | $CH_3(CH_2)_{17}$— | 0.11 |
| 18 | b | R—NH—CO | $CH_3(CH_2)_{11}$— | 0.3 |
| 19 | a | R—CO | $CH_3(CH_2)_{10}$— | 0.12 |
| 20 | a | R—CO | $CH_3(CH_2)_{14}$— | 0.1 |
| 21 | a | R—CO | $CH_3(CH_2)_7CH=CH—(CH_2)_7$— | 0.05 |
| 22 | a | R—CO | $CH_3(CH_2)_{16}$— | 0.11 |
| 23 | d | R—NH—CO | $CH_3(CH_2)_{11}$— | 0.05 |
| 24 | e | R—NH—CO | $CH_3(CH_2)_{11}$— | 0.1 |
| 25 | c | R—NH—CO | $CH_3(CH_2)_{11}$— | 0.1 |
| 26 | d | R—NH—CO | $CH_3(CH_2)_{11}$— | 0.18 |
| 27 | d | R—CO | $CH_3(CH_2)_{10}$— | 0.1 |
| 28 | a | R—NH—CO | $CH_3(CH_2)_7$— | 0.11 |
| 29 | a | R—NH—CO | $CH_3(CH_2)_{15}$— | 0.12 |
| 30 | f | R—NH—CO | $CH_3(CH_2)_{11}$— | 0.19 |
| 31 | f | R—NH—CO | $CH_3(CH_2)_{11}$— | 0.13 |

Legend to Table 1

[1] Indication of the type of moiety that SAC is: a = inulin, $\overline{DP} \geq 23$ (INUTEC ® N25)* b = inulin, DP mainly between 2 and 8, $\overline{DP}$ about 4.5 (INUTEC ® H25P)* c = starch hydrolysate, D.E. 2 (Roquette, France) d = starch hydrolysate, D.E. 28 (Roquette, France) e = starch hydrolysate, D.E. 47 (Roquette, France) f = inulin, $\overline{DP}$ of about 13 (INUTEC ® N10)*
*INUTEC ®: trade name of ORAFTI, Belgium
[2] Indication of the main structure of the hydrophobic moiety (-M) that is attached to SAC.
[3] Meaning of the R-indicator as given in the column headed (-M)
[4] Average degree of substitution s Preferably, $S_{AC}$ in formula (I) represents an inulin moiety derived from chicory inulin with a number-averaged degree of polymerisation ($\overline{DP}$) ranging from 20 to 30.

If it is meant herein to refer to both a fructan and to a starch hydrolysate, they are referred to as particular polysaccharide; similarly, if it is meant herein to refer to both a hydrophobically modified fructan and a hydrophobically modified starch hydrolysate, they are referred to as particular hydrophobically modified polysaccharide.

In a preferred embodiment of the invention, step b) is carried out by treating the substrate with a mixture of compounds, in particular with a mixture of a fructan, preferably inulin, and a hydrophobically modified fructan, preferably hydrophobically modified inulin. In this embodiment, the weight ratio between the fructan and the hydrophobically modified fructan may vary between wide ratios; the said ratio is preferably at least 1:100, 2:100, 5:100, 10:100, 20:100, 30:100, 50:100, or 100:100. The said ratio is preferably at most 100:1, 100:2, 100:5, 100:10, 100:20, 100:30, or 100:50.

It was found, surprisingly, that if the substrate is treated in step b) with a mixture of fixative compounds whereby the mixture contains a particular polysaccharide and a particular hydrophobically modified polysaccharide, that the olfactory effects are not only stronger but also longer-lasting, as compared to known methods for providing fragrance to a substrate and even as compared to methods according to the invention wherein not a mixture of fixative compounds is used. Preferably in this embodiment, the mixture of fixative compounds is a mixture of inulin and a hydrophobically modified inulin. An alternatively preferred mixture is that of a starch hydrolysate and a hydrophobically modified starch hydrolysate. A further preferred mixture is that of a starch hydrolysate and a hydrophobically modified inulin. Yet another preferred mixture is that of inulin and a hydrophobically modified starch hydrolysate.

In one main embodiment of the invention, steps a) and b) are carried out within the framework of the washing of textile. Textile that is (to be) subjected to a washing cycle is herein referred to by its common name laundry.

By laundry is thus meant herein textile fabrics (to be) washed, namely woven as well as non-woven textile made from natural fibres of plant origin, such as cellulose fibres, including cotton, flax and sisal, and of animal origin, including wool and silk, artificial fibres such as cellulose-derived fibres, for example viscose, rayon and cellulose-acetate, and synthetic fibres, for example polyamides, polyesters, polyacrylic fibres, polyethylene and polypropylene fibres, and any mixtures thereof.

By fragrances and perfumes are meant herein pure olfactory compounds as well as mixtures of such compounds and finished blends of same that provide to laundry a desirable scent. Said compounds, mixtures and finished blends are all suitable for the present invention. Typical examples include coumarin, geraniol, linalool, citronellol, and compositions with a scent of lily of the valley, jasmine, lilac, cedar- and sandal wood, amber, fruits and/or musk.

By washing cycle is meant herein a cycle embracing all common steps used for washing laundry, carried out by hand and/or by a machine, typically including (i) a treatment of the laundry with a laundry detergent composition with possibly a soaking step, and rinsing, yielding the so-called wash-waters, (ii) possibly a subsequent treatment with a laundry softener composition and rinsing, yielding the so-called rinsing waters, and (iii) a drying step of the washed and rinsed laundry, either or not including wringing or centrifugation, typically carried out by means of a drier and/or by drying on the air.

In a possible variant of the washing cycle, the laundry is not subjected to a treatment with a laundry detergent composition, but is only subjected to a treatment with a laundry softener composition, followed by a drying step. Such treatment is for example applied in case the laundry is not dirty and one only wants to refresh the textile fabric and/or give it a fresh fragrance. Such method variant is also included herein in the term washing cycle.

As is common in a washing cycle, the fragrance-containing composition is a laundry detergent composition and/or a laundry softener composition. Typically, such laundry detergent compositions and laundry softener compositions contain from 0.001 wt. % to 3 wt % of fragrance. According to this embodiment of the invention, the fixative compound or mixture of fixative compounds is included in the laundry detergent composition and/or in the laundry softener composition in a total amount ranging from 0.005 to 5 wt. %—based on the total combined weight of laundry detergent composition and laundry softener composition. Preferably, the fixative compound or mixture of fixative compounds is/are during the washing cycle not provided in the form of a fragrance-containing film or sheet.

In view of the above, the invention also relates to a laundry composition containing a fragrance, whereby the laundry composition is present in the form of a laundry detergent composition or a laundry softener composition or a kit of parts containing a laundry detergent composition and a laundry softener composition, whereby the laundry composition comprises a fixative compound or mixture of fixative compounds selected from the group consisting of a fructan, a starch hydrolysate preferably having a D.E. ranging from 1 to 50, a hydrophobically modified fructan, and a hydrophobically modified starch hydrolysate.

In another main embodiment of the invention, the invention is not carried out within the framework of the washing of textile, but is simply meant to impart fragrance to a substrate. One way of implementing this is by utilising a fragrance-containing composition in liquid form, whereby the liquid fragrance-containing composition is then sprayed onto the substrate. In this case, the substrate can still be textile but can also be any other type of substrate that can accept a fragrance, such as wood or paper-based substrates like for example letters, tissues or moist tissues/wipes. According to the invention, the fixative compound or mixture of fixative compounds is likewise brought into contact with the substrate in step b). One way of implementing this is by means of adding the fixative compound or mixture of fixative compounds to a liquid fragrance-containing composition.

The invention thus also relates to a paper product, containing a fragrance and a fixative compound or mixture of fixative compounds selected from the group consisting of a fructan, a starch hydrolysate preferably having a D.E. ranging from 1 to 50, a hydrophobically modified fructan, and a hydrophobically modified starch hydrolysate.

In yet another main embodiment of the invention, the invention is not carried out within the framework of the washing of textile, but is meant to impart fragrance to the hair or skin of a mammal, preferably during washing, bathing or showering. Preferably, the method according to the invention comprises the step of treating hair and/or skin with a fragrance-containing composition, whereby said fragrance-containing composition further contains a fixative compound or mixture of fixative compounds selected from the group consisting of:

a fructan;
a starch hydrolysate having a dextrose equivalent ranging from 1 to 50;
a hydrophobically modified fructan; and
a hydrophobically modified starch hydrolysate.

Preferably, a mixture of fixative compounds is contained in the fragrance containing composition, said mixture containing:

a hydrophobically modified fructan plus either a fructan or a starch hydrolysate having a dextrose equivalent ranging from 1 to 50; or
a hydrophobically modified starch hydrolysate plus either a fructan or a starch hydrolysate having a dextrose equivalent ranging from 1 to 50.

Preferably, the fragrance-containing composition is a bathing composition such as a bathing gel, a shower composition such as a shower gel, or a shampoo. These products are as such known; the fixative compound or mixture of fixative compounds can be simply added to an existing formulation, in amounts of preferably at most 5, 4 or 3 wt. %, or even in amounts of preferably at most 2, 1, 0.5 or even 0.1 wt %.

It was found, furthermore, that the fragrance-fixation activity onto the skin of mammals such as humans or companion animals is advantageously influenced in case the fragrance-containing composition as a whole contains both a fructan and a hydrophobically modified fructan whereby the weight ratio between the fructan and the hydrophobically modified fructan varies between 1:100 and 100:1. An example of a suitable fructan is inulin, such as Inutec®H25P (supplier: Orafti, Belgium); an example of a suitable hydrophobically modified fructan is Inulin Lauryl Carbamate, such as Inutec®SP1 (supplier: Orafti, Belgium).

In this main embodiment, the preferred substrate is human hair or the hair of a mammal, preferably the hair of a human or of a companion animal such as a dog or a cat.

The industrial applicability of this main embodiment is illustrated by the following four formulations A, B, C and D.

| Formulation A: Natural conditioning shampoo | |
|---|---|
| | % w/w |
| Phase A | |
| Water | QS |
| DMDM Hydantoin | 0.3 |
| INUTEC SP1 | 0.03 |
| INUTEC H25P | 0.27 |
| Ammonium Lauryl Sulfate 30% | 30 |
| Cocamidopropyl Hydroxysultaine | 6 |

-continued

Formulation A: Natural conditioning shampoo

| | % w/w |
|---|---|
| Phase B | |
| PEG-7 Glyceryl Cocoate and PEG-200 Hydrogenated Glyceryl Palmitate | 3 |
| Perfume | 0.5 |
| Phase C | |
| Ammonium Chloride | QS |
| Phase D | |
| Citric Acid | To pH 5-6 |

Formulation B: Natural hydrating shower gel

| | % w/w |
|---|---|
| Phase A | |
| Water | QS |
| Sodium Laureth Sulfate | 35 |
| Cocamidopropyl Hydroxysultaine | 6.5 |
| INUTEC SP1 | 0.03 |
| INUTEC H25P | 0.27 |
| DMDM Hydantoin | 0.3 |
| Phase B | |
| PEG-7 Glyceryl Cocoate and PEG-200 Hydrogenated Glyceryl Palmitate | 3 |
| Perfume | QS |
| Phase D | |
| Citric Acid | To pH 5-6 |

Formulation C: Shampoo

| | % w/w |
|---|---|
| Phase A | |
| Water | 55.9 |
| DMDM Hydantoin | 0.3 |
| Sodium Laureth Sulfate 28% | 25 |
| Decyl Glucoside | 5 |
| Cocamidopropyl Betaine 30% | 10 |
| INUTEC SP1 | 0.03 |
| INUTEC H25P | 0.27 |
| Laureth-2 | 3.5 |
| Phase B | |
| Perfume | 0.5 |
| Phase C | |
| Citric Acid | To pH 5-6 |

Formulation D: Shower gel

| | % w/w |
|---|---|
| Phase A | |
| Water, deionised | 29.9 |
| Polyquaternium-10 (Polymer JR400) | 0.3 |
| INUTEC SP1 | 0.03 |
| INUTEC H25P | 0.27 |
| Phase B | |
| Sodium Laureth Sulfate 28% | 35 |
| Coco Glucoside | 5 |
| Cocamidopropyl Betaine 30% | 8 |
| Water, deionised | 21.2 |
| Phase C | |
| DMDM Hydantoin | 0.3 |
| Perfume | 0.5 |

Comments to the formulations A, B, C and D:
For every formulation, the various phases should be separately prepared and then mixed with the other ones.
QS=quantum sufficit, as much as suffices.
If necessary, the pH values can be adjusted with NaOH or citric acid to achieve the desired value.
If necessary, the viscosity can be adjusted by using sodium chloride.

The invention is illustrated by the following examples, without being limited thereto.

The examples are accompanied by figures.

Figure 2:
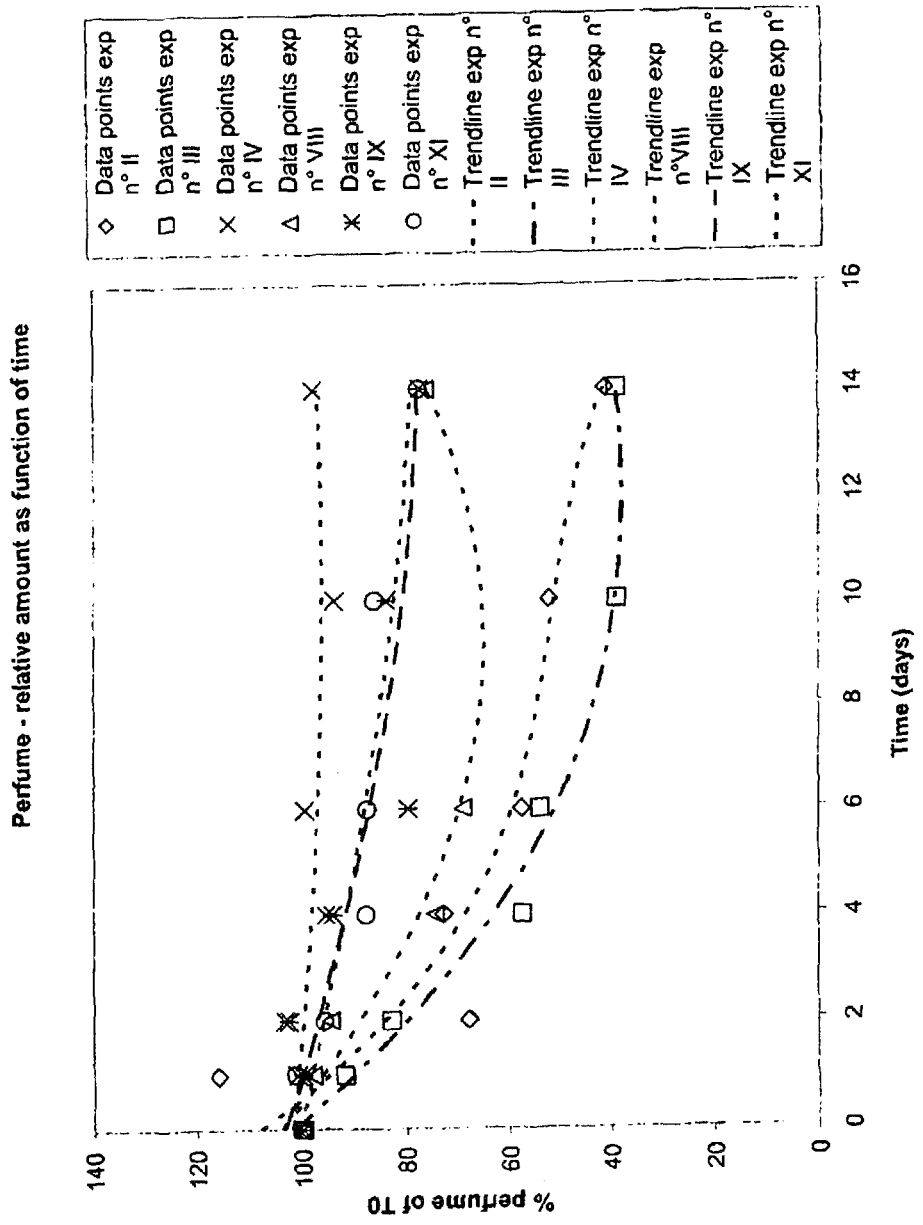

In the figures, FIG. 1 presents a measure of the amount of fragrance adsorbed by laundry samples in different washing cycles and the evolution of said amount as a function of time for the samples stored on the air;

FIG. 2 represents the evolution as a function of time of the amount of fragrance adsorbed in different washing cycles on laundry samples when stored on the air, expressed as percent (%) of the amount at 0 days ($T_0$, i.e. the end of the washing cycle).

GENERAL PROCEDURE

1. Preparation of Laundry Samples 1.1 Preparation of Test Samples of Laundry

Grey bath tissue, composed of 100% cotton, was washed in a standardised manner with a laundry detergent composition without perfume (OMO® Sensitive of Unilever, NL/UK) without the use of a softener composition, in a conventional washing machine at 60° C. and dried for 50 minutes in a conventional drier. The procedure was carried out twice in order to remove the finishes from the bath tissue. Strips were then cut from the tissue (1 cm×8 cm), hemmed to avoid disintegration during the washing cycles, put together in a net-bag, and the above washing cycle was repeated once more. The obtained tissue strips were stored in an air-tight container and named hereinafter test samples.

1.2 Treatment of Test Samples of Launch

Test samples of the laundry have been subjected to the method according to the present invention, namely subjected to a washing cycle with a fragrance-containing laundry composition which furthermore comprises a particular polysaccharide or a particular hydrophobically modified polysaccharide or any combination of both, as defined above. The treatment of the laundry has been carried out in a conventional washing machine at 60° C. and the laundry was dried for 50 minutes in a conventional drier. Details of variants of this general procedure are indicated in the specific examples described below. The test samples treated by a method according to the present invention have been compared with test samples treated by a prior art method.

At the end of the washing cycle, referred to as time $T_0$, the treated test samples obtained were stored in an air-tight vial and analysed.

Similarly treated test samples were exposed to the air at room temperature under standardised conditions for a certain period of time and analysed in order to determine the evolution of the amount of adsorbed fragrance as a function of time.

2. Analysis of the Fragrance Adsorbed on the Laundry

The amount of fragrance adsorbed on a test sample treated during a washing cycle by a method according to the present invention or by a method according to the prior art has been measured via the determination of the amount of fragrance desorbed by the treated test sample under standardised conditions. The determination was made by gas chromatography-mass spectrometry (GC-MS) analysis as detailed below.

2.1 Equipment

GC-apparatus: Agilent Technologies GC 6890N; column: AT-5MS 60 m, 0.25 mm ID; film thickness 0.25 micrometer; detector: Agilent Technologies MS-5973 Inert; injector: CIS 4 Gerstel; autosampler: MPS2 Gerstel; temperature program: 5 minutes (min) at 35° C., then at 5° C./min to 225° C., followed by 10° C./min to 325° C. (run time 53 min); detection: Mass-spectrometer (MS), full scan, EI 70 mV.

2.2 Procedure

A test sample treated by a method according to the invention or treated by a prior art method (reference sample) was, immediately after the end of the washing cycle, weighed and put into a vial which was then air-tight sealed by a rubber cap. After an incubation period of 15 minutes at 125° C., a sample of 2.5 microliter from the headspace of the vial was automatically taken and injected into the GC-MS. The fragrance as such has been analysed too by GC-MS to determine the odorous components of the fragrance.

The identification and quantification of the odorous components of the fragrance present in the headspace of the vials was carried out by means of Chemstation software (Agilent Technologies, formerly Hewlett Packard).

The effects of each method variant used in the washing cycle were analysed by measuring the concentration of the fragrance in the headspace of three vials of test samples that were simultaneously subjected to the same washing cycle. The surface area under the peaks of the main odorous components obtained by CG-MS analysis from the samples was integrated and the sum of the peak areas was calculated and expressed as the total peak area per gram sample, and the mean value resulting from the three analyses, expressed as "area", was taken as a measure for the concentration of the fragrance in the headspace of the vials. This measure is assumed to be directly related to the amount of fragrance adsorbed by the test sample during the washing cycle. Furthermore, following the above procedure, the remaining amount of adsorbed fragrance on similarly treated test samples after different periods of exposure to the air at room temperature under standardised conditions was determined, thus providing data on the evolution of the amount of adsorbed fragrance of the test samples stored on the air as a function of time.

EXAMPLES

Comparative Experiments I to XI

Following the above general procedure, test samples were treated according to the method of the invention with a laundry detergent composition and a laundry softener composition, used in a weight ratio 1/1, either of them containing a particular polysaccharide and/or a particular hydrophobically modified polysaccharide or a combination of both, as detailed in table 2 below.

The results of the analysis of the concentration of the fragrance in the headspace of the vials containing the treated test samples at time $T_0$ (=at the end of the washing cycle and the start of storage period) and at time $T_{14}$ (=storage for 14 days at room temperature on the air), are indicated in table 2 below.

Furthermore, the evolution of the adsorbed fragrance of test samples stored on the air at room temperature over a period of 14 days, was determined as indicated above and the results are presented in FIG. 1, (expressed as "area", namely as the total peak area of the adsorbed fragrance per gram sample, versus time), and in FIG. 2, (expressed in percent (%) of the adsorbed fragrance at time $T_0$ versus time).

TABLE 2

| Ex./ | | | | Amount of perfume[5] | | |
|---|---|---|---|---|---|---|
| Exp.[1] | Detergent[2] | Softener[3] | Perfume[4] | $T_0$ | $T_{14}$ | % at $T_{14}$[6] |
| I* | ✓ | — | 0 | 3 | | |
| II* | ✓ | ✓ | 0.3 | 25 | 10 | 41 |
| III* | ✓ | ✓ | 3 | 235 | 92 | 39 |
| IV | ✓ + 0.2% SP1 + 2% H25P | ✓ | 0.3 | 64 | 62 | 98 |
| V | ✓ | ✓ + 0.2% SP1 + 2% H25P | 0.3 | 50 | 29 | 59 |
| VI | ✓ + 0.2% SP1 | ✓ | 0.3 | 27 | 20 | 74 |
| VII | ✓ + 2% H25P | ✓ | 0.3 | 29 | 26 | 91 |
| VIII | ✓ | ✓ + 0.1% SP1 + 1% H25P | 0.3 | 67 | 51 | 76 |
| IX | ✓ | ✓ + 0.02% SP1 + 0.2% H25P | 0.3 | 85 | 66 | 77 |
| X | ✓ + 0.1% SP1 + 1% H25P | ✓ | 0.3 | 30 | 20 | 67 |
| XI | ✓ + 0.02% SP1 + 0.2% H25P | ✓ | 0.3 | 73 | 57 | 78 |

Legend to Table 2

*I, II and III are comparative experiments; IV to XI are Examples according to the invention ✓ The check mark positively indicates the presence of detergent and softener

[1]Number of the Example/Comparative Experiment, carried out according to the general procedure with the indicated variations

[2]OMO sensitive: laundry detergent without perfume, (trade name of Unilever, NL/UK); weight ratio detergent/softener is 1/1

[3]Softener T600: trade name of Matis Specialties, Belgium, for a standard softener composition essentially comprising quat. ammonium ethoxysulphate [90%] 15%; hydroxyethylcellulose 0.3%; and water ad 100%

[4]Perfume Laundry soft 354427-B (trade name, Luzi AG, Switzerland) for a mixture comprising coumarin, geraniol, butylphenyl methylpropional, linalool, citronellol and alpha-isomethyl ionone); weight percentage as added to the Softener

[5]The amount of perfume is expressed in the $T_0$ and $T_{14}$ columns in total peak area ("area") from perfume components according to the general method above

[6]Remaining perfume after 14 days ($T_{14}$) compared to $T_0$ determined by the general method above, expressed as percentage (%) of the value at $T_0$ SP1: refers to INUTEC ® SP1 (trade name) for inulin ($\overline{DP}$ from 23 to 27) laurylcarbamate, available from Orafti, Belgium), H25P: refers to INUTEC ® H25P (trade mark of Orafti, Belgium, for inulin in powder form containing ≧93.2% w/w on dry matter inulin of DP 2 to 9, and in total maximally 6.8% w/w on dry matter of glucose, fructose and saccharose).

From the above experimental data (Table 2, FIG. 1 and FIG. 2) it clearly follows that, compared to laundry that has not been treated by a method of the present invention, the treatment of textile fabrics during a washing cycle according to the method of the present invention with a particular polysaccharide or a particular hydrophobically modified polysaccharide, defined above, or preferably a combination of both, efficiently provides, through a convenient method, fragrance to laundry, including improved fragrance transfer from a laundry composition to the laundry, improved adsorption, namely improved fixation of the fragrance to the laundry, and improved long-lasting olfactory effects to the laundry which typically last for at least 14 days.

The improved long-lasting fragrance shown in FIG. 2 (by the slower decrease of the amount of adsorbed fragrance as a function of time) for textile samples treated by the method of the present invention and exposed to the air (examples IV, VIII, IX and XI), compared to reference example II, clearly indicates that by the method of the present invention, the adsorption of the fragrance from the laundry composition onto the textile fabric has been improved, inter alia that the method has provided an improved fixation of the fragrance to the laundry.

Furthermore, the data of Table 2 show that, compared to the prior art (exp. no II), the method of the present invention wherein only a particular polysaccharide (exp. VII) or only a particular hydrophobically modified polysaccharide (exp. VI) has been used, provides already an improved transfer of fragrance to the laundry and/or an improved long-lasting fragrance, and that the transfer of fragrance and the long-lasting fragrance is even much more pronounced when in the method of the invention a combination of the particular polysaccharide and the particular hydrophobically modified polysaccharide is used (exp. IV, V, VIII to XI).

Examples XII to XV

The experimental procedure as carried out in Examples IV to XI was repeated, whereby the amount and composition of fixative compound(s) was as given in Table 3. Also in Table 3 the results are provided, expressed in % retention of perfume after 14 days (% at $T_{14}$).

TABLE 3

| Ex. | Detergent | Softener | Rest-amount of perfume (% at $T_{14}$) |
|---|---|---|---|
| XII | ✓ + 0.2% H25P + 0.02% MC | ✓ | 98 |
| XIII | ✓ + 0.2% N25 + 0.02% SP1 | ✓ | 87 |
| XIV | ✓ + 0.2% DE2 + 0.02% SP1 | ✓ | 100 |
| XV | ✓ + 0.2% H25P + 0.02% IE | ✓ | 100 |

Legend to Table 3
The legend to Table 2 applies insofar as applicable. The softener contained 0.3% perfume in all examples. In addition, the following terms are explained below:
H25P: refers to INUTEC H25P
MC: refers to a maltodextrine (DE 2) which has been hydrophobically modified through a carbamate linkage with a C12 alkyl
DE2: refers to a maltodextrine of DE2 (Glucidex, supplier: Roquette)
IE: refers to an inuline having a $\overline{DP}$ of 23 which has been hydrophobically modified through an ester linkage with a C12 alkyl The results in Table 3 clearly demonstrates that a superior fixation and retention of perfume as compared to the comparative experiments has been achieved.

Example XVI

The provision of desirable long-lasting olfactory effects provided by the method of the invention compared to a prior art method has been further illustrated by the sniff test described hereafter.

Procedure Applied for the Sniff Test.

Washing-gloves (100% cotton) named 'A', 'B' or 'C' were treated by the method of the invention according to the conditions indicated in table 2:
gloves A: conditions of exp. II, (0.3% perfume in softener; no SP1; no H25P) (comparative)
gloves B: conditions of exp. IV, (0.3% perfume in softener; 0.2% SP1 and 2% H25P in the detergent composition)
gloves C: conditions of exp. V, (0.3% perfume in softener; 0.2% SP1 and 2% H25P in the softener composition).

The treated gloves were stored for 4 weeks on the air and then presented to a panel of 20 people. The people had to indicate which of the gloves presented the best long-lasting fragrance. The results were as follows:
Number of panel members who indicated gloves A: 0
Number of panel members who indicated gloves B: 13
Number of panel members who indicated gloves C: 7.

It is concluded from the sniff test that the improved olfactory effects imparted to the laundry by the method of the invention are long-lasting.

Example XVII

The perfume-fixative effects of various compounds on cotton wipes was investigated. Wipes (100% cotton) were impregnated with a cleansing lotion. The composition of the lotion was as follows: water (81.35%), Preservative Parmetol A28 S from supplier Schülke & Mayr (0.10%), Ethyl Alcohol denat 96% (15%), PEG-40 Hydrogenated Castol Oil (2.40%), perfume (0.80%). Furthermore 0.35% of a mixture of fixating compounds was added to the lotion. The mixture of fixating compounds contained 55 wt. % INUTEC H25P, 5.5 wt. % INUTEC SP1, the balance being water.

After the wipes had been impregnated with the lotion, the wipes were sealed. This procedure was followed for three different perfumes: "Musky Bouquet", "Citron Simple", and "Marinas". Supplier of all three perfumes is Luzi.

As Reference, wipes were used that had been impregnated with the same lotion, except that no mixture of fixating compounds had been added.

In order to evaluate the effectiveness of the fixating compounds, the wipes were taken out of the packaging, left to rest and evaluated 14 days later. The evaluation consisted of requesting a panel of 10 persons to establish by means of smelling whether the quality of perfume retention of the wipes that had been impregnated with a lotion that contained the mixture of fixating compounds was less, equal, better or much better than the reference wipes. The results are presented in Table 4.

TABLE 4

| Comparison to Reference | Perfume | | |
|---|---|---|---|
| | MB | CS | MA |
| Less | 1 | 1 | 2 |
| Equal | 1 | 0 | 0 |
| Better | 5 | 1 | 1 |
| Much better | 3 | 8 | 7 |

Legend to Table 4
MB Musky Bouquet
CS Citron Simple
MA Marinas

The results clearly show that the wipes according to the invention were able to hold the perfume for a significantly longer time than the reference wipes.

Example XVIII

Various swatches of textile were subjected to a sniff test by a panel of 10 test persons, to establish how good a certain type of perfume had been fixated to the swatch during a washing cycle. The same rating system as in Example XVII was used. The washing cycle was done as described above in section 1.1 of the General procedure. If a fixative compound was used, then this was a mixture of Inutec SP1 and Inutec H25P, which were added to the Omo Sensitive washing powder in amounts of 0.1% (Inutec SP1) and 1% (Inutec H25P). No fixative compounds were added to the softener. The swatches varied in type of textile; furthermore, various perfumes were tested for each type of textile. The perfumes were added to the Omo Sensitive. The perfumes originated from Luzi AG, except for the Clean Burst perfume which is made by Church & Dwight. The test was done 14 days after the washing cycle had been executed. The results are given in Tables 5, 6 and 7.

TABLE 5

Results for "Hibiscus Rosewood"

| Comparison to reference | Textile type | | | |
|---|---|---|---|---|
| | Cotton | Linen | Synthetic | Jeans |
| Less | 1 | 1 | 1 | 0 |
| Equal | 6 | 1 | 4 | 2 |
| Better | 1 | 7 | 4 | 6 |
| Much better | 3 | 1 | 1 | 2 |

TABLE 6

Results for "Yellow Summer"

| Comparison to reference | Textile type | | | |
|---|---|---|---|---|
| | Cotton | Linen | Synthetic | Jeans |
| Less | 1 | 0 | 2 | 0 |
| Equal | 1 | 2 | 1 | 8 |
| Better | 6 | 5 | 3 | 1 |
| Much better | 2 | 3 | 4 | 1 |

TABLE 7

Results for "Clean Burst"

| Comparison to reference | Textile type | | | |
|---|---|---|---|---|
| | Cotton | Linen | Synthetic | Jeans |
| Less | 1 | 0 | 1 | 0 |
| Equal | 1 | 3 | 3 | 2 |
| Better | 3 | 5 | 4 | 5 |
| Much better | 5 | 2 | 2 | 3 |

The results clearly show that the current invention is applicable to various types of substrates, and to various types of perfumes too.

The provision of fragrance to laundry by the method of the invention during a washing cycle is generally suitable for providing desirable fragrance, particularly long-lasting fragrance, to woven and non-woven textile fabrics made from natural fibres of plant origin, such as cellulose fibres, including cotton, linen, flax and sisal, and fibres of animal origin, including wool and silk, artificial fibres such as cellulose-derived fibres, for example viscose, rayon and cellulose-acetate, and synthetic fibres, for example polyamides, polyesters, polyacrylic fibres, polyethylene and polypropylene fibres, and any mixtures thereof.

Furthermore, as a result of said improved fragrance transfer and improved fixation of said fragrance onto laundry provided by the method of the invention compared to the prior art, a larger amount of the total amount of fragrance provided to the washing cycle by the laundry composition is adsorbed by the laundry and also an improved long-lasting fragrance is provided. These improvements clearly result on the one hand in technical and economical advantages.

On the other hand, said improved transfer and improved absorption/fixation of the fragrance onto laundry provided by the method of the invention also enable to reduce the amount of fragrance provided via the laundry composition to the washing cycle, while nevertheless obtaining the same odorous effects at the end of the washing cycle compared to a prior art method wherein initially more fragrance is provided via the laundry composition but of which more of it is lost during the washing cycle via the washing and rinsing waters. These improvements too result in technical and economical advantages.

Example XIX

In this Example, the provision of a fragrance to human hair as substrate with a shampoo as fragrance-containing composition was tested. Two shampoos—coded SH-I and SH-R—were prepared, having compositions as indicated in Table 8.

TABLE 8

| Ingredient | SH-I | SH-R* |
|---|---|---|
| Water | 48 | 48.3 |
| Euxyl K500 | 1 | 1 |
| Neoderm LSH | 3 | 3 |
| Ungerol N28 | 45 | 45 |
| NaCl | 2 | 2 |
| Cool Celsius | 0.7 | 0.7 |
| INUTEC H25P | 0.27 | — |
| INUTEC SP1 | 0.03 | — |

Legend to Table 8
*indicates a comparative experiment, not according to the invention
Euxyl K500 is a preservative composed of Aqua, Diazolidinyl Urea, Sodium Benzoate en Potassium Sorbate; supplier Schulke&Mayr
Neoderm LSH is composed of Aqua, PEG-200 Hydrogenated Glyceryl Palmitate, and PEG-7 Glyceryl Cocoate
Ungerol N28 is a trade name for Sodium laureth sulphate
Cool Celsius is a perfume; supplier Luzi The shampoos were used by a test person in the normal fashion. Subsequently, the fragrance was verified by a test panel, by smelling the hair both 5 minutes and also 30 minutes after application and then rating the strength of presence of any perfume on the hair. Ratings possible were: 'no perfume detectable anymore'; 'weak'; 'acceptable', and 'strong'.

The results were that hair treated with SH-R (comparative experiment) rated 'weak' after 5 minutes and 'no perfume detectable anymore' after 30 minutes. By contrast, hair treated with SH-I (according to the invention) rated 'strong' after 5 minutes and 'acceptable' after 30 minutes.

The invention claimed is:

1. A method for providing fragrance to a substrate, comprising the steps of:
   a) treating the substrate with a fragrance-containing composition; and
   b) treating the substrate with a fixative compound or mixture of fixative compounds selected from the group consisting of:
      a fructan; and
      a hydrophobically modified fructan,
   having the formula (I)

$$S_{AC}(\text{-M})_s \qquad (I)$$

wherein
SAC represents:
   an inulin moiety with a degree of polymerisation (DP) ranging from 2 to 100;

(-M) represents a hydrophobic moiety, substituting at least one hydrogen atom of a hydroxyl group of $S_{AC}$, whereby (-M) is selected from the group consisting of:
- an alkylcarbamoyl radical of formula $R_1$—NH—CO—,
- an alkenyl-carbamoyl radical of formula $R_2$NH—CO—,
- an alkylcarbonyl radical of formula $R_1$—CO—,
- an alkenylcarbonyl radical of formula $R_2$—CO—,
- an alkyl radical of formula $R_1$—,
- an alkenyl radical of formula $R_2$—, and
- a hydroxyalkyl radical of formula $R_3$—, wherein:
- $R_1$ represents a linear or branched alkyl group with 4 to 22 carbon atoms,
- $R_2$ represents a linear or branched alkenyl group with 4 to 22 carbon atoms, and
- $R_3$ represents a linear branched hydroxyalkyl group with 4 to 22 carbon atoms of formula —CHR'—CHOH—R", wherein R' is hydrogen or a linear or branched alkyl radical and R" is a linear or branched alkyl radical; and
- s represents the number of hydrophobic moieties (-M) attached to $S_{AC}$, expressed as the number average degree of substitution (av.DS) per monomeric unit contained in $S_{AC}$ and which ranges from 0.01 to 1.0:

whereby step b) may be executed prior to, simultaneously with, and/or subsequent to the execution of step a), and wherein when the substrate is a textile, steps a) and b) are carried out during a washing cycle.

2. The method according to claim 1, wherein in step b) the textile is treated with a mixture of a fructan and a hydrophobically modified fructan, whereby the weight ratio in the mixture between the fructan and the hydrophobically modified fructan varies between 1:100 and 100:1.

3. The method according to claim 1, wherein the fructan is inulin with a degree of polymerisation (DP) ranging from 2 to 100.

4. The method according to claim 1, wherein the fragrance-containing composition comprises from 0.001 wt. % to 3 wt. % of fragrance and is a laundry detergent composition and/or a laundry softener composition, wherein the fixative compound or mixture of fixative compounds is included in the laundry detergent composition and/or in the laundry softener composition in an amount ranging from 0.005 to 5 wt. % based on the total weight of laundry detergent composition and laundry softener composition.

5. The method according to claim 4, wherein the fixative compound or mixture of fixative compounds is/are not provided in the form of a fragrance-containing film or sheet.

6. The method of claim 1, wherein in formula (I) $S_{AC}$ represents an inulin moiety derived from chicory inulin with an average degree of polymerisation ($\overline{DP}$) ranging from 20 to 30.

7. The method according to claim 1, wherein the substrate is the skin or the hair of a mammal, and wherein in step b) the skin or hair is treated with a mixture of fixative compounds containing:
i) a fructan, and
ii) a hydrophobically modified fructan, whereby the weight ratio in the mixture between
i) and ii) varies between 1:100 and 100:1.

8. The method according to claim 7, wherein steps a) and b) are carried out simultaneously, wherein the mammal is a human or a dog or a cat, and wherein the fragrance-containing composition is a shower gel, a bathing gel, or a shampoo.

9. The method according to claim 3, wherein the substrate is a paper-based substrate.

10. The method according to claim 1, wherein the substrate is a paper-based substrate.

* * * * *

UNITED STATES PATENT AND TRADEMARK OFFICE
CERTIFICATE OF CORRECTION

PATENT NO.       : 8,496,994 B2                                    Page 1 of 1
APPLICATION NO.  : 12/596798
DATED            : July 30, 2013
INVENTOR(S)      : Levecke It is certified that error appears in the above-identified patent and that said Letters Patent is hereby corrected as shown below:

References Cited, FOREIGN PATENT DOCUMENTS, title page, Col. 2, line 5, for EP 1 614 743, "11/2003" should be --1/2006--.

References Cited, FOREIGN PATENT DOCUMENTS, title page, Col. 2, line 8, for EP 1 541 117, "6/2008" should be --6/2005--.

In the Claims

Claim 1, Col. 17, line 17, "linear branched" should be --linear or branched--.

Signed and Sealed this
Nineteenth Day of August, 2014

Michelle K. Lee
*Deputy Director of the United States Patent and Trademark Office*